United States Patent
Al Azri

(10) Patent No.: US 10,191,025 B2
(45) Date of Patent: Jan. 29, 2019

(54) MEDICAL DEVICE, MEDICAL SYSTEM AND METHOD FOR DETECTING DISEASES

(71) Applicant: Sultan Sultan Hamad Mohammed Al Azri, Abu Dhabi (AE)

(72) Inventor: Sultan Sultan Hamad Mohammed Al Azri, Abu Dhabi (AE)

(73) Assignee: Al Azri, Sultan Sultan Hamad Mohammed, Al Bahya, Abu Dhabi (AE)

( * ) Notice: Subject to any disclaimer, the term of this patent is extended or adjusted under 35 U.S.C. 154(b) by 0 days.

(21) Appl. No.: 15/569,751

(22) PCT Filed: Apr. 27, 2016

(86) PCT No.: PCT/GB2016/051190
§ 371 (c)(1),
(2) Date: Oct. 26, 2017

(87) PCT Pub. No.: WO2016/174427
PCT Pub. Date: Nov. 3, 2016

(65) Prior Publication Data
US 2018/0128802 A1 May 10, 2018

(30) Foreign Application Priority Data

Apr. 27, 2015 (GB) .................................. 1507137.6

(51) Int. Cl.
*G01N 33/00* (2006.01)
*G01N 1/22* (2006.01)
(Continued)

(52) U.S. Cl.
CPC ....... *G01N 33/0075* (2013.01); *G01N 1/2273* (2013.01); *G01N 1/26* (2013.01);
(Continued)

(58) Field of Classification Search
CPC .. G01N 33/0075; G01N 1/2273; G01N 21/39; G01N 33/497; G01N 1/26; G08B 21/02
See application file for complete search history.

(56) References Cited

U.S. PATENT DOCUMENTS

| 4,499,377 A | 2/1985 | Presser |
| 5,842,326 A * | 12/1998 | Wolf ....................... B65B 55/02 |
| | | 53/425 |

(Continued)

FOREIGN PATENT DOCUMENTS

| EP | 1 480 413 A1 | 11/2004 |
| EP | 2 703 049 A2 | 3/2014 |

(Continued)

OTHER PUBLICATIONS

UKIPO Combined Search and Examination Report dated Jul. 15, 2015, from GB application No. 1507137.6.

(Continued)

*Primary Examiner* — Ryan W Sherwin
(74) *Attorney, Agent, or Firm* — Foley & Lardner LLP

(57) ABSTRACT

The present invention provides a medical device to provide an alert of the potential detection of a disease in an infrastructure having a chamber of air and a geographic location, the device comprising: one or more sample ports of known sub-location within the infrastructure, the one or more sample ports being open to a designated part of the infrastructure and a sample of air from the air chamber being operable to pass through the one or more sample ports; a detector to receive the sample of air from a specific one of the one or more sample ports and being operable to generate molecular characteristic data for identifying diseases from the sample of air; a processor operable to analyze the molecular characteristic data from the sample of air; and an alert module operable to issue an alert output in response to (Continued)

the detection of particular molecular characteristic data from the sample of air.

16 Claims, 5 Drawing Sheets

(51) Int. Cl.
  *G01N 1/26* (2006.01)
  *G01N 21/39* (2006.01)
  *G01N 33/497* (2006.01)
  *G08B 21/02* (2006.01)

(52) U.S. Cl.
  CPC ............ *G01N 21/39* (2013.01); *G01N 33/497* (2013.01); *G08B 21/02* (2013.01)

(56) References Cited

U.S. PATENT DOCUMENTS

| | | |
|---|---|---|
| 2003/0069002 A1 | 4/2003 | Hunter et al. |
| 2005/0190058 A1 | 9/2005 | Call |
| 2007/0068284 A1 | 3/2007 | Castro et al. |
| 2008/0074660 A1* | 3/2008 | Ye et al. .................. G01J 3/00 356/300 |
| 2009/0053989 A1 | 2/2009 | Lunde et al. |
| 2009/0072968 A1 | 3/2009 | Levesque et al. |
| 2010/0289653 A1 | 11/2010 | Calio et al. |
| 2013/0174646 A1 | 7/2013 | Martine |

FOREIGN PATENT DOCUMENTS

| | | |
|---|---|---|
| FR | 2993364 A1 | 1/2014 |
| JP | H0480631 A | 3/1992 |
| WO | WO-98/046978 A1 | 10/1998 |
| WO | WO 00/079243 A1 | 12/2000 |
| WO | WO-2007/008955 A3 | 1/2007 |
| WO | WO-2008-086094 A3 | 7/2008 |
| WO | WO-2008/108792 A2 | 9/2008 |
| WO | WO-2011/003941 A1 | 1/2011 |

OTHER PUBLICATIONS

UKIPO Examination Report dated Dec. 31, 2015, from GB application No. 1507137.6.

International Search Report dated Jul. 18, 2016, for PCT/GB2016/051190.

* cited by examiner

MEDICAL DEVICE, MEDICAL SYSTEM AND METHOD FOR DETECTING DISEASES

This invention relates to a medical device for detecting diseases and to a corresponding system and method of detecting diseases.

BACKGROUND TO THE INVENTION

Many diseases are transmitted by viruses or bacteria in the air, i.e. airborne viruses or bacteria. Airborne bacteria, viruses and other micro-organisms are a common cause of diseases or ailments, particularly in the human respiratory system. Examples of airborne viruses include measles, influenza (flu), smallpox and chickenpox. Examples of airborne bacterial diseases include tuberculosis, bacterial meningitis and pneumonia. Another example of an air-carried disease is Legionnaires disease where the bacterium is carried in water droplets which are inhaled by a human whilst showering.

An influenza epidemic in the 15th century in Europe had an almost 20% mortality rate. In the 19th century, influenza killed over 25 million people in Spain. Airborne diseases could only travel as first as the wind that carried them and many of the viruses or bacteria, if airborne for a long time, no longer cause harm.

In the present day and age airborne diseases can travel vast distances in favourable environmental conditions which give the viruses or bacteria the capacity to cause harm to humans for longer periods. Aircraft, trains, cars and ferries, particularly mechanisms for mass transport or public transport are designed to transport humans in comfort but, at the same time, ironically offer an excellent environment for airborne diseases to maintain their capacity for harming humans for longer, thereby facilitating the geographical spread of diseases.

Infected people or the breath they exhale are each sources by which disease can be transmitted and infected people may not necessarily be showing signs of illness, symptoms, when travelling.

During the 2003 SARS epidemic, some countries initiated temperature screening at points of entry, i.e. in airports and ferry passenger terminals. In 2001, the US Postal Service was used to send parcels containing anthrax with five people dying and many others becoming infected.

"Cavity-enhanced optical frequency comb spectroscopy: application to human breath analysis" Michael J. Thorpe, David Balslev-Clausen, Matthew S. Kirchner, and Jun Ye—Optics Express, Vol. 16, Issue 4, pp. 2387-2397 (2008)) discloses a technique for detecting molecules in human breath that may be biomarkers for diseases.

It is an object of the present invention to provide a medical device and system to detect and/or reduce the spread of diseases whether introduced naturally or artificially into the bio-environment.

Accordingly, the present invention provides a medical device to provide an alert of the potential detection of a disease in an infrastructure having a chamber of air and a geographic location, the device comprising:
  one or more sample ports of known sub-location within the infrastructure, the one or more sample ports being open to a designated part of the infrastructure and a sample of air from the air chamber being operable to pass through the one or more sample ports;
  a detector to receive the sample of air from a specific one of the one or more sample ports and being operable to generate molecular characteristic data for identifying diseases from the sample of air; and
  a processor operable to analyse the molecular characteristic data from the sample of air; and an alert module operable to issue an alert output in response to the detection of particular molecular characteristic data from the sample of air.

The present invention also provides a method of detecting a disease in an infrastructure having a chamber of air and a geographic location, comprising:
  receiving sample air from a sample port located in a sub-location of the infrastructure;
  analysing the sample air and generating molecular characteristic data of the sample air from the sub-location;
  analysing the molecular characteristic data to detect particular molecular characteristic data from the sample air; and
  reporting the results of the analysis together with the geographic location of the infrastructure and the sub-location from which the sample air was taken.

The present invention further provides a device, system and method as claimed.

The present invention can be considered environmentally-friendly as it can detect diseases that are harmful to humans, other animals, plants and/or other lifeforms.

BRIEF DESCRIPTION OF THE PRESENT INVENTION

In order that the present invention may be more readily understood, it will now be described, by way of example, with reference to the accompanying drawings, in which.

DETAILED DESCRIPTION OF THE PRESENT INVENTION

A medical device embodying the present invention comprises a mechanism for detecting airborne diseases within an infrastructure, such as an aircraft, in one example, having or enclosing a volume of air in which humans reside for a period of time, either whilst being transported or in a place of work, study, leisure or repose. The infrastructure defines a large plenum or chamber of air.

The air in the infrastructure chamber may be still, passively passing through the chamber and/or being actively circulated, recirculated and/or filtered. In the foregoing example, the infrastructure is an aircraft and the infrastructure chamber is the aircraft's pressurised cabin.

Figure 1:
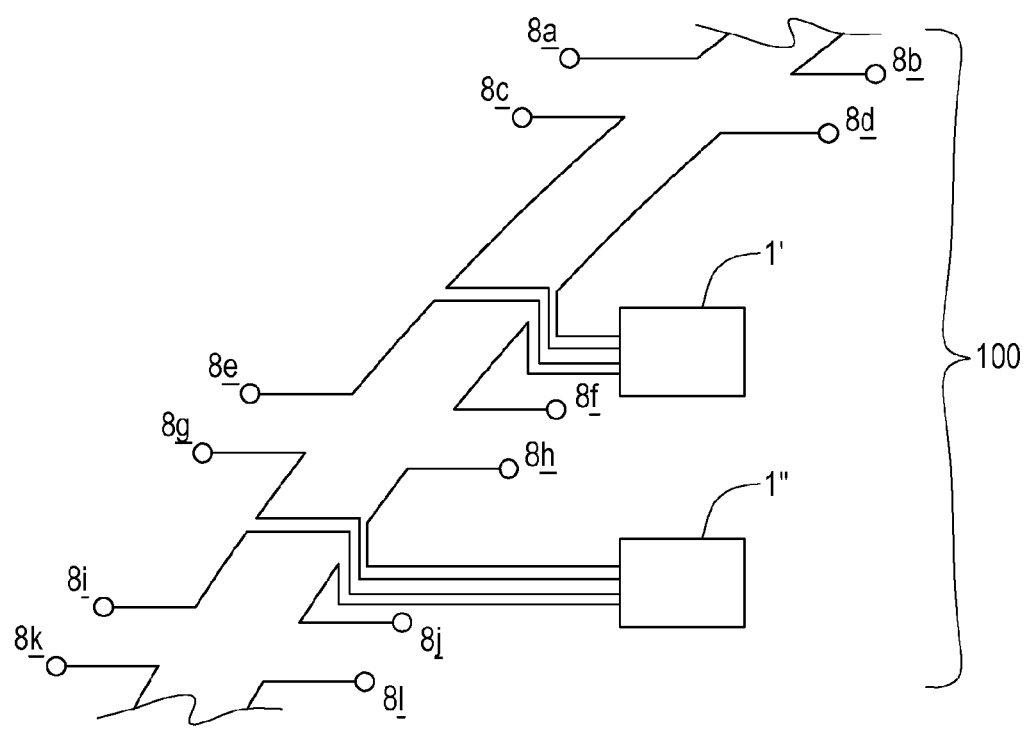
FIG. 1 is a schematic representation of a medical system incorporating at least two medical devices embodying the present invention.
Figure 2:
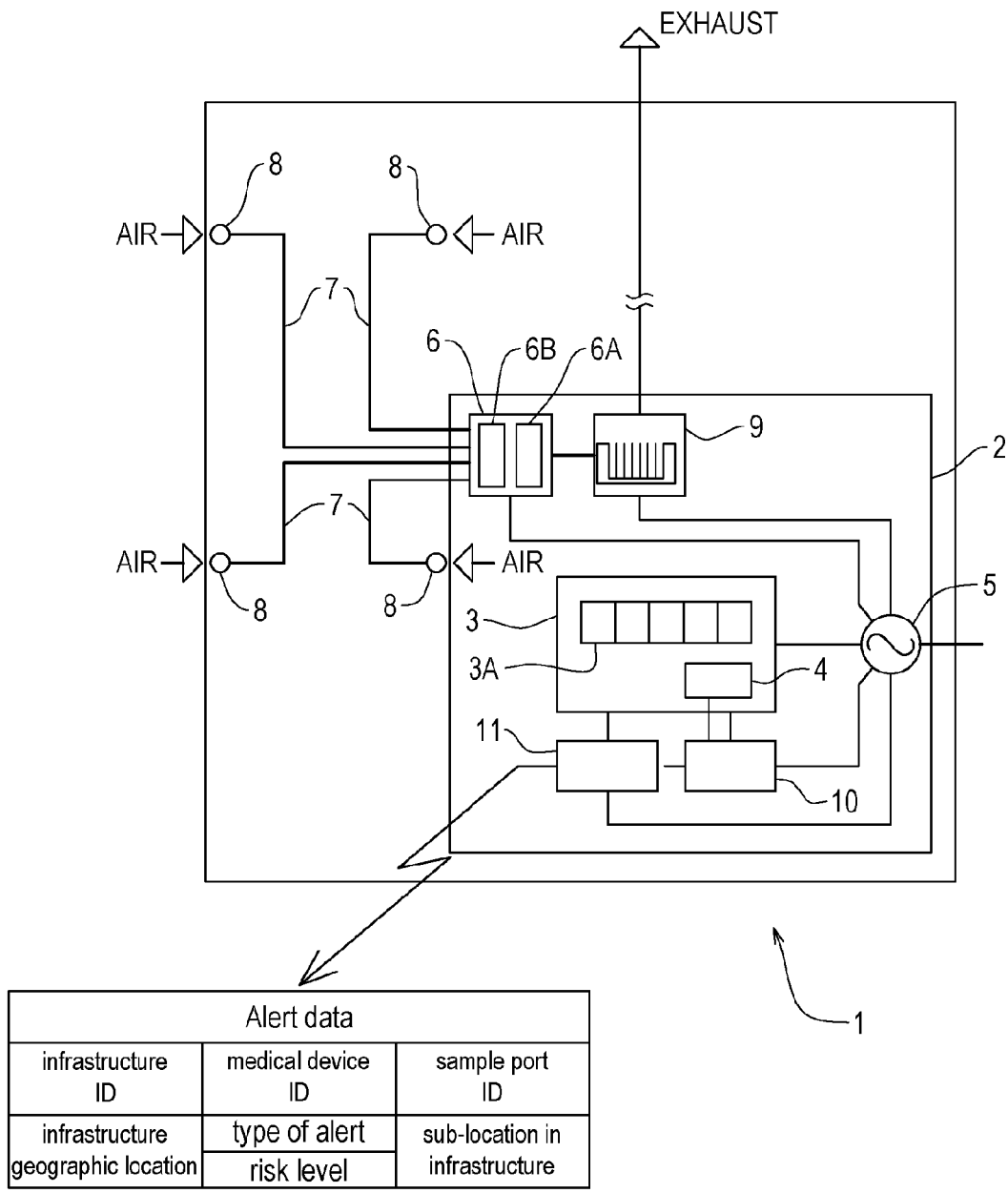
FIG. 2 is a schematic representation of a medical device embodying the present invention.

Referring to FIGS. 1 and 2, a medical device 1 embodying the present invention is at the hub of a medical system 100. The medical device 1 comprises a housing 2 enclosing a central processor unit module 3 with a data storage module 4, a power supply module 5, a sampler module 6 with an air mover 6A, such as a fan, and a filter 6B. The sampler module 6 obtains samples of air from the volume of air via an array of conduits or ducts 7, each terminating in an inlet port 8 located at a part of the infrastructure where individuals are likely to pass or be located, for example at or around an entry door or at intervals along the cabin. The medical device 1 also has a detector module 9, an alert module 10 and a communication module 11.

The infrastructure can be mobile, i.e. a form of transport, or static, such as a building. Examples of infrastructure are aircraft (the present example), cruise and cargo ships, buses (public, school and workers), trains, large scale worker accommodation, factories and workplaces, schools, hotels, offices, prisons, refuge camps, public waiting areas and in any structure having a ventilation system. The medical system 100 is particularly beneficial for mobile infrastructures such as the exemplary aircraft.

The power supply module 5 is preferably a standalone power supply recharged continuously by the infrastructure's power supply and powers the air mover 6A, the switching of the sampler 6, the detector module 9, the processor 3, the alert module 10 and the communication module 11. The power supply module 5 may be composed of discrete power supplies tailored to supply each of the respective power consuming modules.

Figure 3:
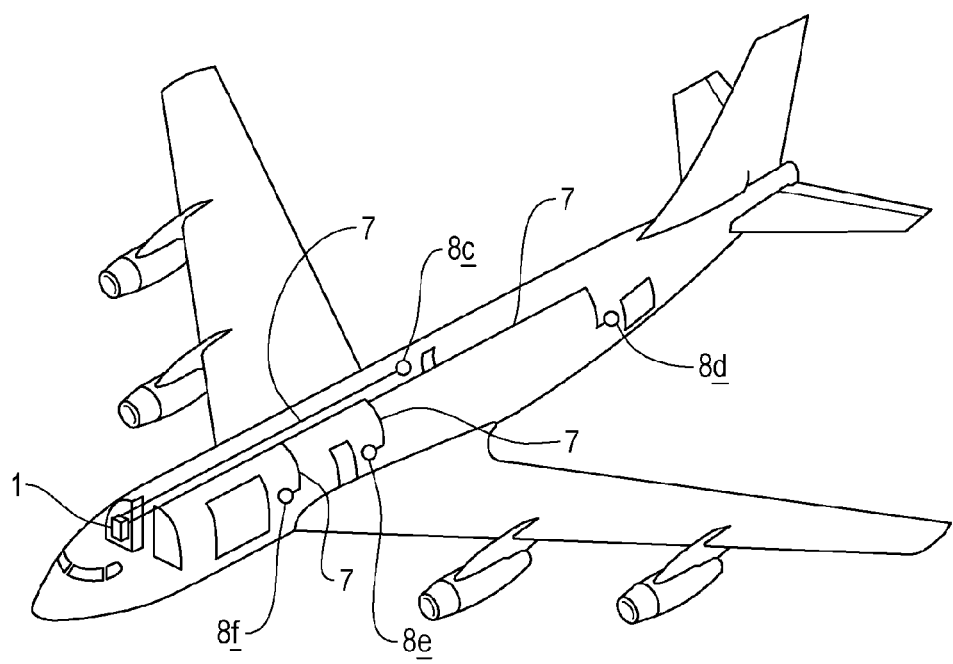
FIG. 3 is a schematic representation of an aircraft fitted with a medical device embodying the present invention.

In the aircraft of FIG. 3, there are four inlet ports 8c, 8d, 8e and 8f. Each inlet port 8 has a unique identifier associating that port to a specific location in the infrastructure. In this example, each inlet port 8 has its unique identifier marked, for example by 1D or 2D barcoding, adjacent the inlet port so that a maintenance engineer can capture the identifier when servicing the medical device.

Referring again to FIGS. 1 and 2, the medical device data storage module 4 maintains a log of inlet ports 8 mapped to their individual locations in the infrastructure. For example, each exit door of an aircraft has its own individual inlet port 8. A good location for inlet ports 8 in an aircraft is also within a toilet cubicle—a sub-location in an aircraft where an individual is alone for a period of time and can therefore be distinguished from others on the aircraft.

Alternatively, or in addition, each section of the cabin of the aircraft has its own individual inlet port 8 so, for example, seat rows 1 to 5, 6-10, 11-15 . . . each have their own associated inlet port 8. Inlet ports 8 are each associated with or allocated to a known sub-location, or zone, within the aircraft, the infrastructure.

The air is drawn into each of the ducts 7 through the inlet ports 8, which are at known sub-locations around the aircraft, by the sampler's air mover 6A. The sampler module 6 has a staged filter 6B which feeds the switched air samples into the detector module 9 in which molecules are counted and characterised. A first filter stage removes all macroscopic dust and dirt from the air sample and a second filter stage removes ultrafine particles so as to introduce filtered to keep the optical and active components in the downstream detector 9 free of contamination.

The sampler module 6 switches samples of air from one respective duct 7 at a time past or through the detector module 9. The detector module is operable to identify airborne diseases in the sampled air from the aircraft cabin. The detector module 9 is exposed to selected air samples from known locations around the aircraft. The sampled air is then exhausted from the detector, preferably to outside the volume of air from which the sample was taken (to prevent reintroduction in another sub-location of the sampled air. In effect, this means expelling the sampled air to the outside atmosphere or at least outside the aircraft's pressurised cabin in this example.

The detector module 9 counts and characterises molecules from each filtered air sample. The processor and data storage modules use the molecular characteristic data derived by the detector module 9 to determine a likely identity of a detected molecule. Molecular characteristics include but are not limited to measurement of the density and concentration level. Molecular characteristics can also be detection of markers for viruses or bacteria and not the virus or bacteria itself but a marker molecule (or combination of molecules) expressed by the virus or bacterium.

Typical sampling intervals are 1, 2, 3 or 5 minutes (as required). That is: air samples from one duct/inlet port combination 7,8 are fed to the detector 9 for a fixed duration before being switched to another duct/inlet port combination 7,8. The data storage module is continuously updated with the identity of the duct/inlet port combination 7,8 currently being sampled and hence the sub-location in the aircraft from which the sample originates is known to the medical device and is logged in the data storage module along with time and date information and any other relevant auxiliary data.

Preferably, the detector module 9 utilises optical frequency comb spectroscopy, a technique developed by Therope, Ye et al. from the National Institute and Technology and the University of Colorado ("Cavity-enhanced optical frequency comb spectroscopy: application to human breath analysis" Michael J. Thorpe, David Balslev-Clausen, Matthew S. Kirchner, and Jun Ye—Optics Express, Vol. 16, Issue 4, pp. 2387-2397 (2008)). Such techniques detect molecules that may be biomarkers for diseases and "sort through" all the molecules in human breath contained in the air samples presented to the detector. The technique is sensitive enough to distinguish infrequently occurring (rare) molecules, which are present only in trace quantities.

Different molecules vibrate and rotate at certain distinct resonant frequencies that depend on the molecule's composition and structure—i.e. different molecules have different molecular characteristics which can be detected by the detector module 9. A laser-based molecular characteristic detector, using for example the optical comb technique, allows for many different gases to be analysed and detected simultaneously with high sensitivity through their interaction with the laser in the laser chamber of the detector module 9. Other laser molecular detection systems and non-laser molecular detection systems are available but laser-based molecular detection systems offer an elegant solution to continuously scanning interleaved or switched air samples.

The optical frequency comb technique offers a highly reliable laser-based technique to collect data and characterise molecules to determine diseases in an air sample with an attached confidence level. The optical frequency comb utilises a very precise laser which then measures different colours, spectra, frequencies and intensities of light. Each comb is tuned to a distinctive frequency of a particular molecules vibration or rotation and the entire comb covers a broad spectral range so as to generate molecular characteristic data for the analysed air sample.

The medical device 1 further comprises an alert module 10 to provide an external output from the device notifying of the detection of a potential disease source. The processor module 3 is in communication with an aircraft's GPS or other geolocation device to determine the location of the medical device 1 at any given time. For static infrastructures, the medical device's location is pre-programmed into the medical device 1 so that the geographic location of the medical device 1 can be transmitted with an alert together with sub-location data which triggered the alert. Sub-location information of the medical device 1 is logged as this provides more granular location information of the particular inlet port 8 from which a disease has been sampled. For example, inlet port 8h is identified as being the source of a sample containing a strain of influenza. Inlet port 8h is mapped, for example, in the data storage module 4, as being located in a sub-location of the aircraft corresponding to this aircraft's seat rows 21-25—a sub-location within the infrastructure. The aircraft's location or position is known from the aircraft's GPS as being on approach to London's Heathrow airport. Thus, the medical device 1 provides the location of the infrastructure, on approach to Heathrow, and a sub-location of from where in the infrastructure the disease was first sampled—an individual likely in seat rows 21-25.

The resulting alert from the alert module 10 is immediately processed and presented by a local display 3A and/or remote display. There are various levels of alert thresholds such as (Green/Safe/OK, Alert, Action, Disease Identified, Critical Disease Identified, Unknown Alert). The alert threshold levels are programmed to react to indicators such as molecular characteristics, sensitivity, density, zones of detection.

In the example of FIG. 2, the alert data output by the alert module 10 comprises: an infrastructure identifier, a medical device or system identifier, an inlet port identifier, the geographic location of the infrastructure, the sub-location in the infrastructure which triggered the alert, the type of alert and the risk level associated with the alert. Alert data can comprise selected ones of this data and/or additional data.

The medical device 1 also comprises a communication module 11 to establish, in some examples, a communication link to remote services. Each of the modules 3, 4, 5, 6, 9 provides the medical system with a service or functionality.

The processor module 3 is programmed to analyse the molecular characteristic data generated from the air samples in the closed environment of the detector module 9. The medical device 1 continually feeds air samples into the detector module 9 and, at intervals, switches the air sample supply between inlet ports 8. The detector module 9 produces molecular characteristic data relating to the identity or at least characteristics of the molecules in each air sample. The molecules may be viruses, bacteria, biomarkers and/or analytes. The processor module 3 runs a software based analysis on the molecular characteristic data collected from the detector module 3.

Figure 4:
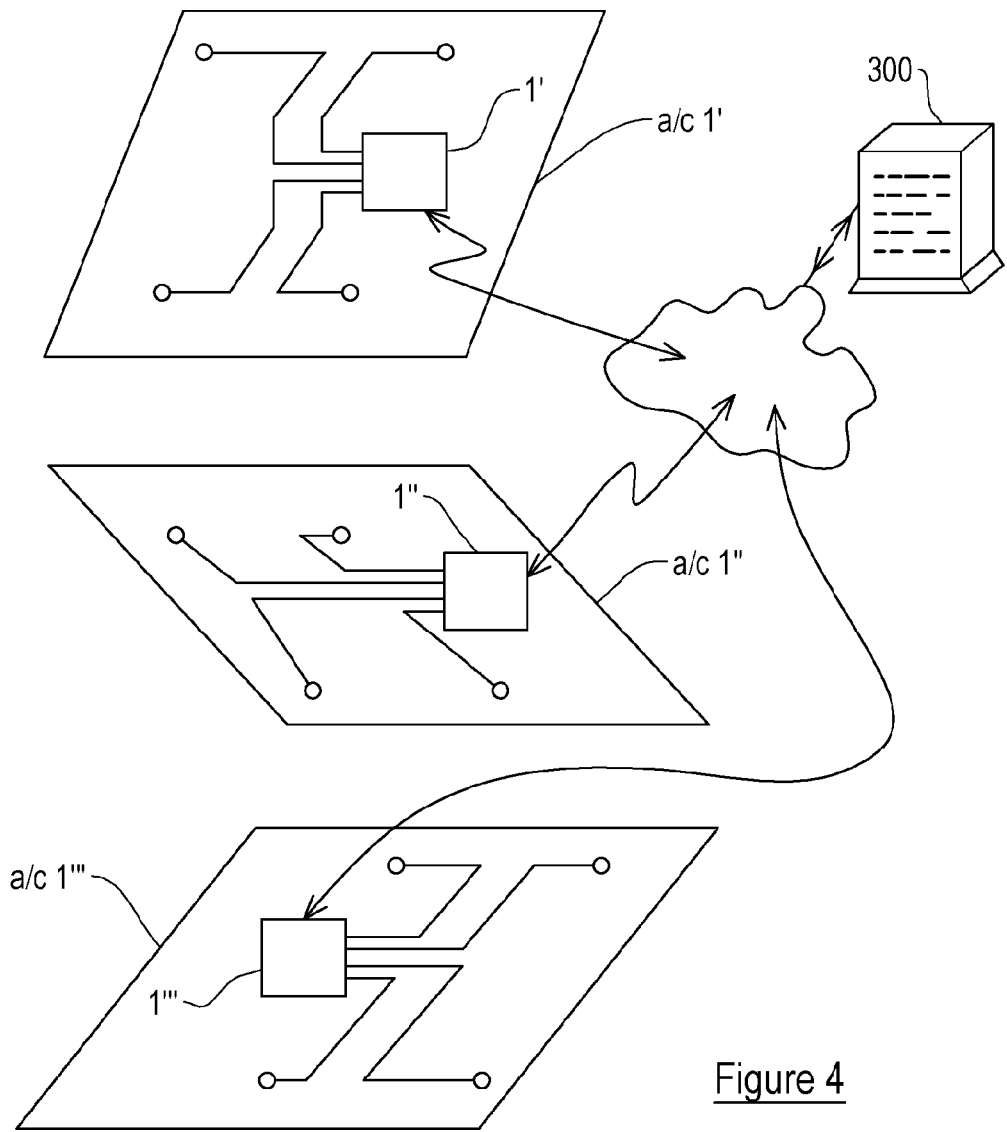
FIG. 4 is a schematic representation of multiple medical devices embodying the present invention deployed in multiple aircraft and in communication with a control centre.

Data, such as new information linking a biomarker having certain molecular characteristics to a particular disease or associating the biomarker's molecular characteristics to a certain risk level, from laboratories and health organisations around the world is collated and sent to the medical devices 1, see FIG. 4, from respective control centres 300. The data updates the data storage modules 4 with information about airborne diseases, new strains of bacteria or viral mutations and links between molecular characteristic data and airborne diseases and their associated risk levels.

The molecular characteristic data generated at a control centre 300 level and at a medical device 1 or system 100 level, feeds a dataset of relationships between diseases, risk levels and molecular characteristics which is continually being refined and adapted to represent the most up to date state of knowledge. Artificial intelligence and heuristic models are used to enhance the dataset and the updates provided to medical devices helping the medical devices 1 and systems 100 to identify previously undiscovered trends or links.

Update data is transmitted to various infrastructures, for example aircraft a/c1', a/c1" and a/c1''', which are within range of the transmitting control centre 300, see FIG. 4.

The medical devices 1 are also programmed to detect 'alien' or unknown molecular characteristics and raise an alert in response to an unidentified or uncharacterised molecule. An uncharacterised molecule is a detected molecule whose characteristics do not fit with any known molecules or the detected molecule expresses characteristics associated, matching or correlating with characteristics of a known harmful virus or bacterium or biomarker therefor.

In examples, the medical devices 1 use baselines from normal ambient patterns to monitor "normal" historical characteristic patterns in the sampled molecular characteristic data and to identify changes in the patterns of the molecular data collected by the detector modules 9. This provides, at least, early alert data that there is something unusual being sampled.

The inlet ports 8 and the associated modules are installed unobtrusively. The data readings from the detector modules 9 are transmitted, for example, locally, hardwired, or remotely by wireless technologies. The medical devices are preferably integrated into the infrastructure's sub systems or comprise an infrastructure sub-system.

For aircraft, the control centre 300 is in the airport/control tower or for ships, the control centre 300 is at nominated port centres and for buildings, the local authorities or emergency services have responsibility. As well as providing updates to the medical devices 1, the control centres 300 may also have responsibility for reacting to an alert output from a medical device 1 in the control centre's locale.

The medical devices 1 preferably transmit critical disease information such as the type of disease, the location (GPS location of an aircraft, for example), the granular sub-location (a range of seat rows in the aircraft, for example), sample date and time, the medical device's serial number, registry information and other atmospheric analysis.

The medical device 1 is integrated with the aircraft (or other infrastructure) communication system to create a direct communication channel to a pre-designated control centre 300 which is operable to plan an emergency response if the medical device 1 sends a disease alert. The response may be containment, quarantine, treatment or even a refusal to grant landing rights.

The medical devices 1 embodying the present invention empower the control centre to respond proactively.

Figure 5:
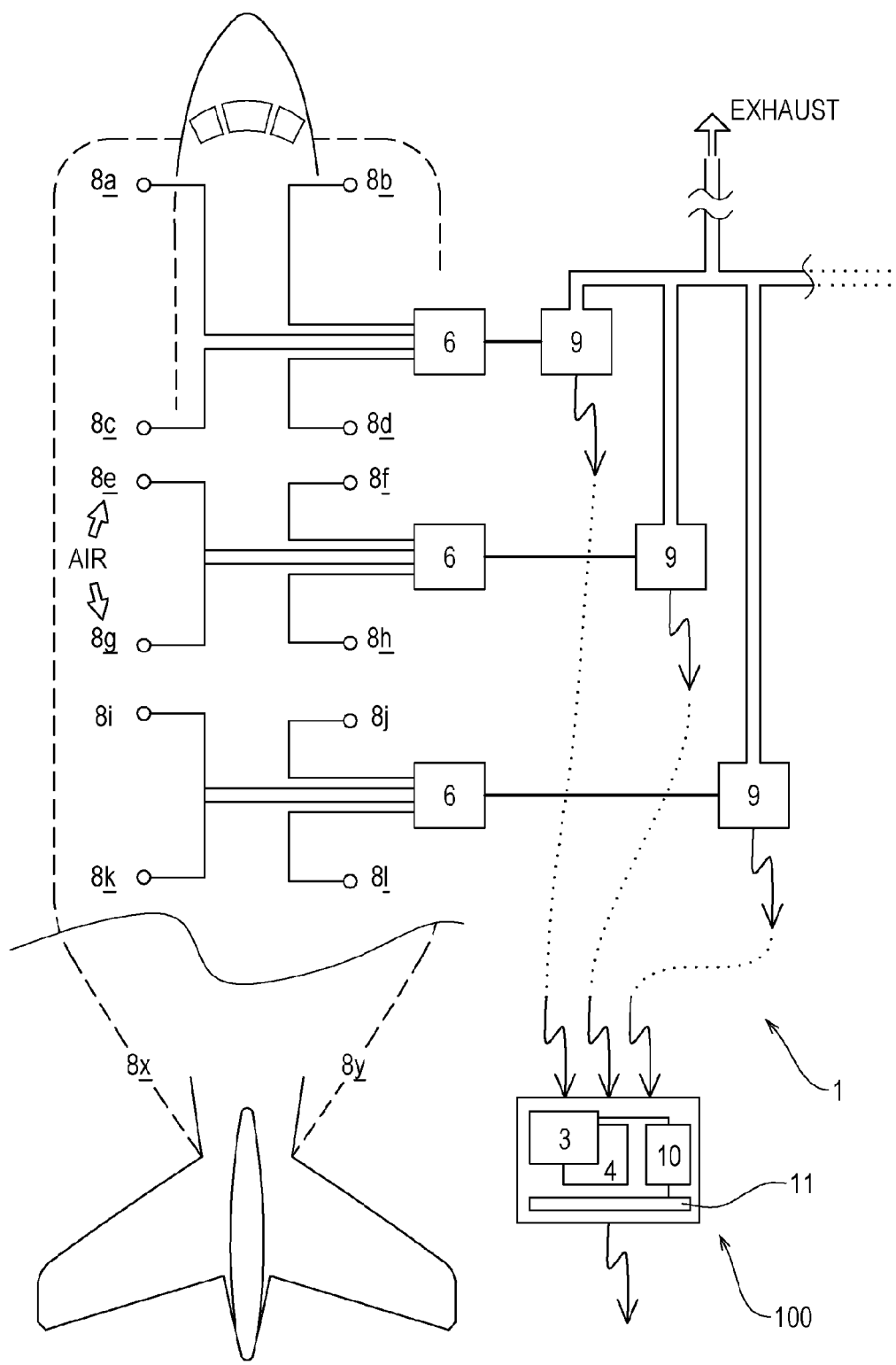
FIG. 5 is a schematic representation of a medical system embodying the present invention.

Referring to FIG. 5, in some examples, the medical device 1 is one of a network of medical devices 1', 1" comprising a medical system 100 installed in an infrastructure, in this example, an aircraft. The module services are provided by dedicated units distributed within the network of medical devices 1, each dedicated unit comprising an above-described module. In the FIG. 5 example, the central processor 3, the data storage module 4, the alert module 10 and the communication module 11 are common. All of the other modules: the sampler module 6 and the detector module 9 are distributed about the network and are associated with their respective duct and inlet systems 7, 8.

In other examples, the functions of the medical device 1 performed by the respective modules are distributed over the network of medical devices.

In one example, there is a central hub providing the module services via respective modules for the or each medical device 1 in the network. In another example, there are discrete devices, each providing a discrete service, which devices are networked together so that the system 100 is a composite of the medical device modules 1.

In some embodiments, the medical device 1 further comprises a 'treatment' module (not shown) that further processes the sampled air. In preferred embodiments, the processing comprises 'treating' diseases in the air, e.g. by subjecting the air to heating or superheating to reduce contaminants or even fully sterilise it. In some embodiments, the treatment module comprises an autoclave operable to subject the sample air to high pressure (typically 100 kPa above atmospheric pressure) saturated steam at approximately 120° C. or even 140° C. or higher for a predetermined time, generally 5-15 minutes depending on the volume of air. Optionally, the treated air may then be returned into circulation.

Implementation of embodiments of the invention can detect diseases early and forewarn destinations of potentially infected people located in a specific infrastructure, the location of which is known to the medical device 1, and also, the medical device 1 has logged a sub-location of the infrastructure from where an alert was triggered. Detection can take place on boarding an aircraft, when entering or passing through an area fitted with inlet samplers or after a period of time in transit (or in repose in a static infrastructure). Such detection and the composite alert information provided by the medical device 1 enables response services to act proactively.

Such proactive action in response to the medical device's composite alert information may:
- reduce the risk of infectious diseases spreading through travelling populations;
- control the spread of disease by effectively monitoring, detecting and responding to alert information;
- contain the threat of infectious diseases to known locations (in which the disease was detected); and
- create an additional layer of risk mitigation.

When used in this specification and the claims, the term "comprises" and "comprising" and variations thereof mean that specified features, steps or integers and included. The terms are not to be interpreted to exclude the presence of other features, steps or compounds.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realising the invention in diverse forms thereof.

The invention claimed is:

1. A medical device to provide an alert of the potential detection of a gas or a disease in an infrastructure having a chamber of air and a geographic location, the device comprising:
   one or more sample ports of known sub-location within the infrastructure, the one or more sample ports being open to a designated part of the infrastructure and a sample of air from the air chamber being operable to pass through the one or more sample ports;
   a laser-based molecular characteristic detector to receive the sample of air from a specific one of the one or more sample ports and being operable to generate molecular characteristic data for identifying gases or diseases from the sample of air;
   a processor operable to analyse the molecular characteristic data from the sample of air and to issue an alert output in response to the detection of particular molecular characteristic data from the sample of air; and
   a treatment module for treating the sample of air, wherein the treatment module comprises an autoclave, operable to subject the sample of air to high pressure saturated steam at approximately 120° C. or higher.

2. The medical device of claim 1, wherein the infrastructure is a static infrastructure.

3. The medical device of claim 2, wherein the static infrastructure has a geographic location, data of which is available to the medical device.

4. The medical device of claim 1, wherein the infrastructure is a mobile infrastructure.

5. The medical device of claim 4, wherein the mobile infrastructure has a mechanism for identifying the geographic location of the infrastructure and data from the mechanism is available to the medical device.

6. The medical device of claim 1, wherein the alert output comprises composite alert data and the composite alert data comprises geographic location data for the infrastructure; and sub-location data specifying the sub-location within the infrastructure from which the sample of air was taken.

7. The medical device of claim 1, wherein the detector is an optical frequency comb detector.

8. The medical device of claim 1, wherein there are a plurality of sample ports arranged around the infrastructure at designated locations known to the medical device.

9. The medical device of claim 8, wherein each sample port has a unique identifier.

10. The medical device of claim 6, further comprising an air mover to draw air into the or each sample port and downstream to the detector.

11. The medical device of claim 1, wherein a sampler switches the supply of air samples to the detector between respective sample ports so that samples from known sub-locations in the infrastructure are provided to the detector one at a time for analysis, thereby linking a sample of air being analysed in the detector to a sample port of known sub-location in the infrastructure.

12. A medical system to provide an alert of the potential detection of a gas or a disease in an infrastructure having a chamber of air and a geographic location, the system comprising:
   one or more sample ports of known sub-location within the infrastructure, the one or more sample ports being open to a designated part of the infrastructure and a sample one or more samples of air from the air chamber being operable to pass through the one or more sample ports;
   one or more laser-based molecular characteristic detectors, each laser-based molecular characteristic detector to receive a respective one of the one or more samples of air from a specific one of the one or more sample ports and being operable to generate molecular characteristic data for identifying gases or diseases from each sample the respective one or more samples of air;
   a processor operable to analyse the molecular characteristic data from the sample of air and to issue an alert output in response to the detection of particular molecular characteristic data from the sample of air; and
   a treatment module for treating the sample of air, wherein the treatment module comprises an autoclave, operable to subject the sample of air to high pressure saturated steam at approximately 120° C. or higher.

13. The medical system of claim 12, wherein some components of the medical system are allocated to one or more specific sample ports and other components of the medical system are common to the system.

14. The medical system of claim 13, wherein each detector is allocated to one or more specific sample ports and the remaining components of the medical system are common to the system.

15. A method of detecting a gas or a disease in an infrastructure having a chamber of air and a geographic location, comprising:
- receiving a sample of air by a laser-based molecular characteristic detector from a sample port located in a sub-location of the infrastructure;
- analysing the sample of air and generating molecular characteristic data of the sample of air from the sub-location;
- analysing the molecular characteristic data to detect particular molecular characteristic data from the sample of air;
- reporting the results of the analysis together with the geographic location of the infrastructure and the sub-location from which the sample of air was taken; and
- treating the sample of air with a treatment module, wherein the treatment module comprises an autoclave, operable to subject the sample of air to high pressure saturated steam at approximately 120° C. or higher.

16. The method of claim 15, wherein the reporting comprises issuing an alert in response to the detection of particular molecular characteristic data from the sample of air.

* * * * *